US012156722B2

(12) United States Patent
Jones

(10) Patent No.: US 12,156,722 B2
(45) Date of Patent: Dec. 3, 2024

(54) PULSE RATE DETECTION DEVICE AND PULSE RATE DETECTION PROGRAM

(71) Applicant: AISIN CORPORATION, Kariya (JP)

(72) Inventor: Michael Jones, Tokyo (JP)

(73) Assignee: AISIN CORPORATION, Kariya (JP)

( * ) Notice: Subject to any disclaimer, the term of this patent is extended or adjusted under 35 U.S.C. 154(b) by 396 days.

(21) Appl. No.: 17/600,008

(22) PCT Filed: Mar. 27, 2020

(86) PCT No.: PCT/JP2020/014360
§ 371 (c)(1),
(2) Date: Sep. 29, 2021

(87) PCT Pub. No.: WO2020/203912
PCT Pub. Date: Oct. 8, 2020

(65) Prior Publication Data
US 2022/0104717 A1 Apr. 7, 2022

(30) Foreign Application Priority Data

Mar. 29, 2019 (JP) ................. 2019-066379

(51) Int. Cl.
A61B 5/024 (2006.01)
A61B 5/00 (2006.01)
(52) U.S. Cl.
CPC ........ A61B 5/02405 (2013.01); A61B 5/0077 (2013.01); A61B 5/02416 (2013.01)
(58) Field of Classification Search
None
See application file for complete search history.

(56) References Cited

U.S. PATENT DOCUMENTS

2007/0016381 A1* 1/2007 Kamath ............... A61B 5/7207
702/19
2013/0006123 A1* 1/2013 Aoshima ............... A61B 5/1118
600/483
(Continued)

FOREIGN PATENT DOCUMENTS

JP H10-258040 A 9/1998
JP 2013-13644 A 1/2013
(Continued)

OTHER PUBLICATIONS

Jun. 9, 2020 International Search Report issued in International Patent Application No. PCT/JP2020/014360.
(Continued)

Primary Examiner — Katherine L Fernandez
(74) Attorney, Agent, or Firm — Oliff PLC

(57) ABSTRACT

A pulse rate detection device includes: a moving image obtaining device configured to obtain a moving image captured by photographing a body surface of a subject, a pulse rate obtaining device configured to obtain a pulse rate of the subject on the basis of change of a pixel value of the body surface in the moving image, a reliability obtaining device configured to obtain reliability of the obtained pulse rate, and an output device configured to output the obtained pulse rate, if the obtained reliability is equal to or greater than predetermined reliable criteria and, if the obtained reliability is less than reliable criteria and change of the obtained pulse rate is within a predetermined appropriate range.

7 Claims, 14 Drawing Sheets

(56) References Cited

U.S. PATENT DOCUMENTS

| | | | |
|---|---|---|---|
| 2013/0197382 A1 | 8/2013 | Yang | |
| 2014/0276099 A1 | 9/2014 | Kirenko et al. | |
| 2015/0148687 A1 | 5/2015 | Kitajima et al. | |
| 2015/0302158 A1* | 10/2015 | Morris | G06V 10/25 702/19 |
| 2016/0015277 A1 | 1/2016 | Dumoulin et al. | |
| 2017/0112382 A1 | 4/2017 | Nakata et al. | |
| 2017/0238805 A1* | 8/2017 | Addison | A61B 5/743 |
| 2017/0303862 A1 | 10/2017 | Nakamura et al. | |
| 2018/0110428 A1 | 4/2018 | Murakami et al. | |
| 2020/0260052 A1* | 8/2020 | Hutchinson | G06V 20/52 |

FOREIGN PATENT DOCUMENTS

| | | |
|---|---|---|
| JP | 2014-236775 A | 12/2014 |
| JP | 2016-120065 A | 7/2016 |
| JP | 2017-93760 A | 6/2017 |
| JP | 2019-42145 A | 3/2019 |
| WO | 2014002276 A1 | 1/2014 |

OTHER PUBLICATIONS

Teichmann, et al. "Non-contact Monitoring Techniques—Principles and Applications"; Proc. IEEE Eng. Med. Biol. Soc. 34th Ann. Int. Conf., San Diego, CA, USA; 2012; pp. 1302-1205.

U.S. Appl. No. 17/599,945, filed Sep. 29, 2021 in the name of Michael Jones.

Jun. 9, 2020 International Search Report issued in International Patent Application No. PCT/JP2020/014359.

Apr. 26, 2022 Extended Search Report issued in European Patent Application No. 20782721.3.

Apr. 26, 2022 Extended European Search Report issued in Patent Application No. 20782220.6.

Bashar, Syed Khairul et al., "Developing a Novel Noise Artifact Detection Algorithm for Smartphone PPG Signals: Preliminary Results*", IEEE EMBS International Conference on Biomedical & Health Informatics (BHI), (2018), pp. 79-82.

Apr. 23, 2024 Office Action issued in U.S. Appl. No. 17/599,945.

* cited by examiner

FIG.8

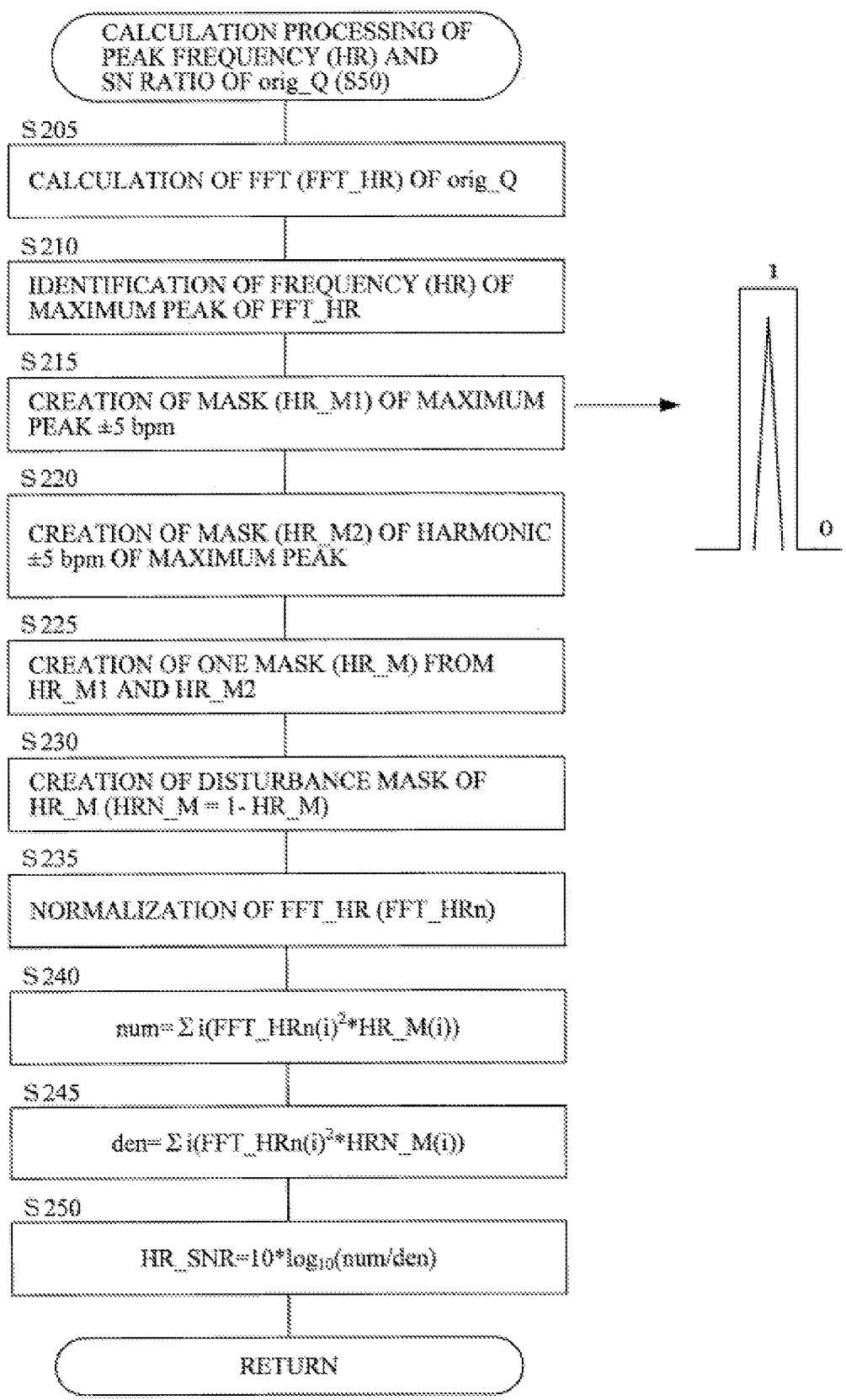

CALCULATION PROCESSING OF PEAK FREQUENCY (HR) AND SN RATIO OF orig_Q (S50)

S205 CALCULATION OF FFT (FFT_HR) OF orig_Q

S210 IDENTIFICATION OF FREQUENCY (HR) OF MAXIMUM PEAK OF FFT_HR

S215 CREATION OF MASK (HR_M1) OF MAXIMUM PEAK ±5 bpm

S220 CREATION OF MASK (HR_M2) OF HARMONIC ±5 bpm OF MAXIMUM PEAK

S225 CREATION OF ONE MASK (HR_M) FROM HR_M1 AND HR_M2

S230 CREATION OF DISTURBANCE MASK OF HR_M (HRN_M = 1 - HR_M)

S235 NORMALIZATION OF FFT_HR (FFT_HRn)

S240 $num = \Sigma i(FFT\_HRn(i)^2 * HR\_M(i))$

S245 $den = \Sigma i(FFT\_HRn(i)^2 * HRN\_M(i))$

S250 $HR\_SNR = 10 * \log_{10}(num/den)$

RETURN

PULSE RATE DETECTION DEVICE AND PULSE RATE DETECTION PROGRAM

TECHNICAL FIELD

The present invention relates to a pulse rate detection device and a pulse rate detection program, and relates to, for example, detection of a pulse rate by image processing.

BACKGROUND ART

It is important to detect a pulse rate in order to grasp a health condition and a physiological state of a subject. Usually, the pulse rate is detected by attaching an instrument to the subject, but there has been a high demand for easily detecting the pulse rate, and therefore technologies for detecting the pulse rate of the subject in a noncontact manner have been actively researched.

This can monitor, for example, a pulse rate of a driver of a vehicle and thereby further promoting traffic safety.

Non Patent Literature 1 discloses such a technology of detecting the pulse rate of the subject in such a noncontact manner. This technology photographs an arm of the subject with a camera, and obtains changes of skin color, brightness, or the like from a camera image to detect the pulse rate. Since the brightness and the color of a body surface change due to blood flow, the pulse rate can be detected by executing image processing of video.

However, when the pulse rate is detected under an environment where there is a disturbance such as the subject moving or environmental light changing, there is a problem that degree of reliability (reliable accuracy) of the detected pulse rate is uncertain.

For example, when a pulse rate is detected for a certain period, 86% of the detections are reliable and rest of the detections are not reliable due to a disturbance, it is uncertain which portion of the detections are reliable.

Moreover, there is also another problem that even if the reliability of the detected value can be evaluated, a period during which the pulse rate can be detected becomes shorter as the evaluation is made more stringent.

CITATION LIST

Non-Patent Literature

Non-Patent Literature 1: "Non-contact monitoring techniques—Principles and applications," D. Teichmann, C. Bruser, B. Eilebrecht, A. Abbas, N. Blanik, and S. Leonhardt, Con. Proc. IEEE Eng., Med. Biol. Soc. 34th Ann. Int. Conf., San Diego, Calif., USA, 2012, pp. 1302-1305.

DISCLOSURE OF INVENTION

Problem to be Solved by the Invention

The object of the present invention is to output a pulse rate that is highly reliable.

SUMMARY OF THE INVENTION(S)

(1) In order to achieve above mentioned object, the exemplary embodiment described in a first aspect provides a pulse rate detection device comprising: a moving image obtaining means configured to obtain a moving image captured by photographing a body surface of a subject; a pulse rate obtaining means configured to obtain a pulse rate of the subject on the basis of change of a pixel value of the body surface in the moving image; a reliability obtaining means configured to obtain reliability of the obtained pulse rate; and an output means configured to output the obtained pulse rate, if the obtained reliability is equal to or greater than predetermined reliable criteria and, if the obtained reliability is less than reliable criteria and change of the obtained pulse rate is within a predetermined appropriate range.

(2) The exemplary embodiment described in a second aspect provides the pulse rate detection device according to the first aspect, wherein the change of the pulse rate is a difference between the obtained pulse rate and an immediate past pulse rate, and the output means outputs the obtained pulse rate as being within the appropriate range if the difference therebetween is equal to or less than predetermined criteria.

(3) The exemplary embodiment described in a third aspect provides the pulse rate detection device according to the first or second aspect, wherein the pulse rate obtaining means obtains the pulse rate from a pulse rate peak in a frequency domain of the obtained moving image, and the reliability obtaining means obtains the reliability on the basis of an SN ratio of the obtained pulse rate.

(4) The exemplary embodiment described in a fourth aspect provides the pulse rate detection device according to the third aspect, further comprising a reducing means configured to reduce the reliability if a disturbance peak in the frequency domain of a disturbance factor that reduces accuracy of the obtained pulse rate is equal to or closer than a predetermined amount to the obtained pulse rate peak.

(5) The exemplary embodiment described in a fifth aspect provides the pulse rate detection device according to the fourth aspect, wherein the disturbance factor is due to a movement of the body surface, and the reducing means reduces the reliability if a movement peak in the frequency domain of the movement of the body surface is equal to or closer than the predetermined amount to the obtained pulse rate peak.

(6) The exemplary embodiment described in a sixth aspect provides the pulse rate detection device according to the fourth or fifth aspect, wherein the disturbance factor is due to variation of light illuminating the body surface, and the reducing means reduces the reliability if a light peak in the frequency domain of the variation of light is equal to or closer than the predetermined amount to the obtained pulse rate peak.

(7) The exemplary embodiment described in a seventh aspect provides a pulse rate detection program for causing a computer to realize: a moving image obtaining function for obtaining a moving image captured by photographing a body surface of a subject; a pulse rate obtaining function for obtaining a pulse rate of the subject on the basis of change of a pixel value of the body surface in the moving image; a reliability obtaining function for obtaining reliability of the obtained pulse rate; and an output function for outputting the obtained pulse rate, if the obtained reliability is equal to or greater than predetermined reliable criteria and, if the obtained reliability is less than reliable criteria and change of the obtained pulse rate is within a predetermined appropriate range.

EFFECT OF THE INVENTION(S)

According to the present invention, a pulse rate that is highly reliable can be outputted by outputting the pulse rate on the basis of reliability.

BRIEF DESCRIPTION OF DRAWINGS

FIG. 8 is a flowchart for describing calculation processing of a peak frequency and an SN ratio of orig_Q.

BEST MODE(S) FOR CARRYING OUT THE INVENTION

(1) Outline of Embodiments

A pulse rate detection device 1 (FIG. 1) evaluates reliability of a detected pulse rate on the basis of an SN ratio of a pulse signal, and evaluates the reliability in consideration of disturbance factors due to movement and light.

The pulse rate detection device 1 has a pulse rate display criteria 1 and a pulse rate display criteria 2 for displaying the pulse rate, wherein the pulse rate display criteria 2 is lower than the pulse rate display criteria 1, wherein when the SN ratio is equal to or greater than the former, the pulse rate is displayed, and when the SN ratio is equal to or greater than the latter and less than the former, the pulse rate is displayed on the condition that the difference from the immediate past pulse rate is smaller than a predetermined reference.

When the SN ratio is less than the pulse rate display criteria 2, the reliability is considered low and the pulse rate is not displayed.

Additionally, the pulse rate detection device 1 takes into account, as the disturbance factors that disrupt the pulse rate detection, a movement disturbance caused by movement of the face of a subject 11 and a light disturbance caused by changes in the light illuminating the face of the subject 11, and when the peak frequency in the frequency domain of the movement disturbance or light disturbance is close to the pulse rate at a value equal to or greater than the predetermined reference, the pulse rate detection device 1 determines that the reliability of the detected pulse rate is low due to these disturbances and does not display the pulse rate.

(2) Details of Embodiments

Figure 1A:
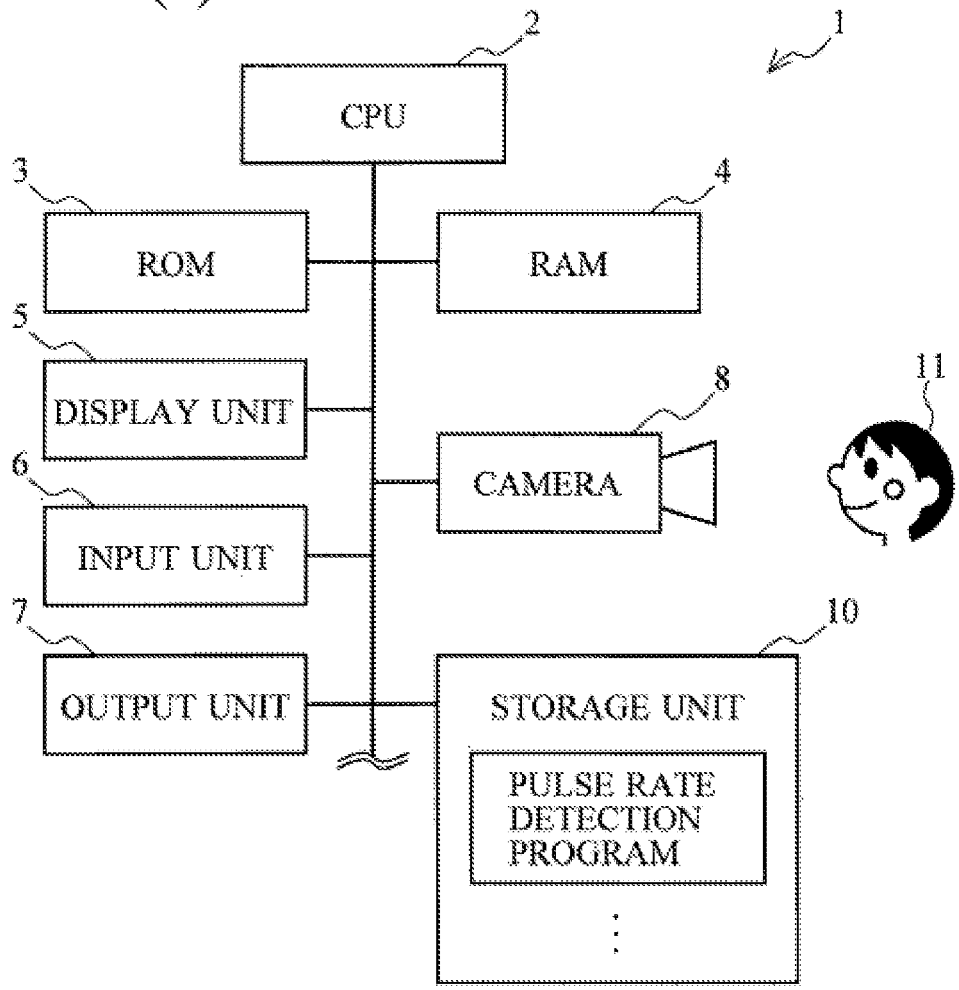
FIG. 1 are diagrams for describing a configuration of a pulse rate detection device.
Figure 1B:
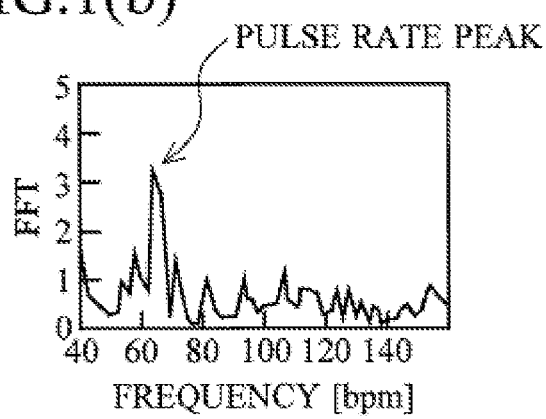

FIG. 1 are diagrams for describing a configuration of a pulse rate detection device 1 of this embodiment.

The pulse rate detection device 1 is mounted on a vehicle, for example, monitors a pulse rate of a passenger (e.g., subject, such as a driver and a passenger in a passenger seat), and grasps physiological states, such as physical condition and a state of tension of the driver.

Moreover, the pulse rate detection device can be used for detecting and monitoring a pulse rate of patients or disaster victims at medical sites, disaster sites, and the like, or installed in homes and commercial facilities for users to easily detecting their pulse rate.

As illustrated in FIG. 1(a), the pulse rate detection device 1 includes a Central Processing Unit (CPU) 2, a Read Only Memory (ROM) 3, a Random Access Memory (RAM) 4, a display unit 5, an input unit 6, an output unit 7, a camera 8, a storage unit 10, and the like, and is configured to detect (and/or estimate and/or measure) a pulse rate of a subject 11.

The CPU 2 is a central processing unit configured to execute various kinds of information processing and controls in accordance with a program stored in the storage unit 10, the ROM 3, and the like.

In the present embodiment, a moving image captured by the camera 8 is image-processed to detect a pulse rate of the subject 11.

Although this detection can be executed in a visible light wavelength region or an infrared region, visible light is used as an example in the present embodiment.

Moreover, lighting configured to illuminate the subject 11 with the visible light or infrared light can also be provided.

The ROM 3 is a read only memory and is configured to store basic programs, parameters, and the like for operating the pulse rate detection device 1.

The RAM 4 is readable and writable memory and is configured to provide a working memory at the time of the CPU 2 operating.

The present embodiment assists the CPU 2 in detecting the pulse wave from a skin portion of an image by developing and storing the image (still image of one frame) that composes a moving image, or by storing calculation results thereof.

The skin portion concerned may be any place where a body surface, such as a face or limb, is exposed, and the pulse rate is detected from a surface of the face (facial surface), as an example, in the present embodiment.

The display unit 5 is composed of a display device, such as a liquid crystal display, and is configured to displays information required for an operation of the pulse rate detection devices 1, such as, an operation screen of the pulse rate detection device 1, a display of the pulse rate, and also attention with regard to reliability of the detected pulse rate.

The input unit 6 is composed of an input device, such as a touch panel, installed to be superimposed on the display device, and is configured to receive an input of various kinds of information depending on whether or not there is a touch on the screen display.

The output unit 7 is an interface configured to output various kinds of information to external devices. For example, the detected pulse rate can be output, or an alarm can be output when a change appears in the pulse rate.

Moreover, the output unit 7 can output the information to other control devices, such as a control unit, that controls the vehicle. The control device that receives the output of the pulse rate from the output unit 7 can determine, for example, drowsiness, a state of tension, and the like of the driver, and can execute controls for the driver, such as vibrating the steering wheel or seat to awaken the driver from drowsiness, and outputting warning sounds or messages.

It is also possible to execute at least one of inter-vehicle distance control, vehicle speed control, or brake control in accordance with a state of tension of the driver, as control for the vehicle, determined on the basis of the detected pulse rate.

For example, when the control device determines that the driver is in a state of high tension exceeding a predetermined value, the control device controls the inter-vehicle distance to be larger than a criteria value and controls the vehicle speed to be equal to or less than a predetermined vehicle speed, and, if the vehicle speed is equal to or faster than a predetermined vehicle speed, executes deceleration processing by automatic brake operation, etc.

A camera 8 is a moving image capturing camera and is composed of an optical system including a lens and an image element that converts the image formed by this lens into an electric signal, and is installed so that near the face of the subject 11 is a position of the photographing screen.

In addition, the camera 8 photographs the moving image in the visible light wavelength region, but when detecting the pulse rate in the infrared region, a camera for infrared rays equipped with an infrared image sensor is used.

The camera 8 photographs the subject 11 at a predetermined frame rate and outputs a moving image composed of these continuous images (continuous still images).

The image concerned is composed of an array of pixels, which is the minimum unit composing the image.

The storage unit 10 is composed of a storage media, such as a hard disk and an Electrically Erasable Programmable Read-Only Memory (EEPROM), and is configured to store a pulse rate detection program used for the CPU 2 to detect the pulse wave, and other programs and data.

Data of the pulse rate detected by the CPU 2 in accordance with the pulse rate detection program is temporarily stored in the RAM 4, and is output to the outside or stored in the storage unit 10, as required.

The pulse rate detection program is a program that causes the CPU 2 to execute the pulse wave detection processing.

By executing the pulse rate detection program, the CPU 2 executes information processing, such as setting of a measurement area in the image, detection of the pulse rate, evaluation of the reliability of the detected pulse rate, and output control of the pulse rate according to the reliability thereof.

FIG. 1(*b*) illustrates an example of detection of a pulse rate.

When a signal Q containing a pulse wave component is transformed by Fast Fourier Transform (FFT), a pulse rate peak appears near 60 bpm (beats per minute). This is derived from change of a skin color of the subject 11 due to the pulse, and this is the detected value of the pulse rate of the subject 11.

A similar pulse rate peak can be obtained even using infrared brightness.

Figure 2:
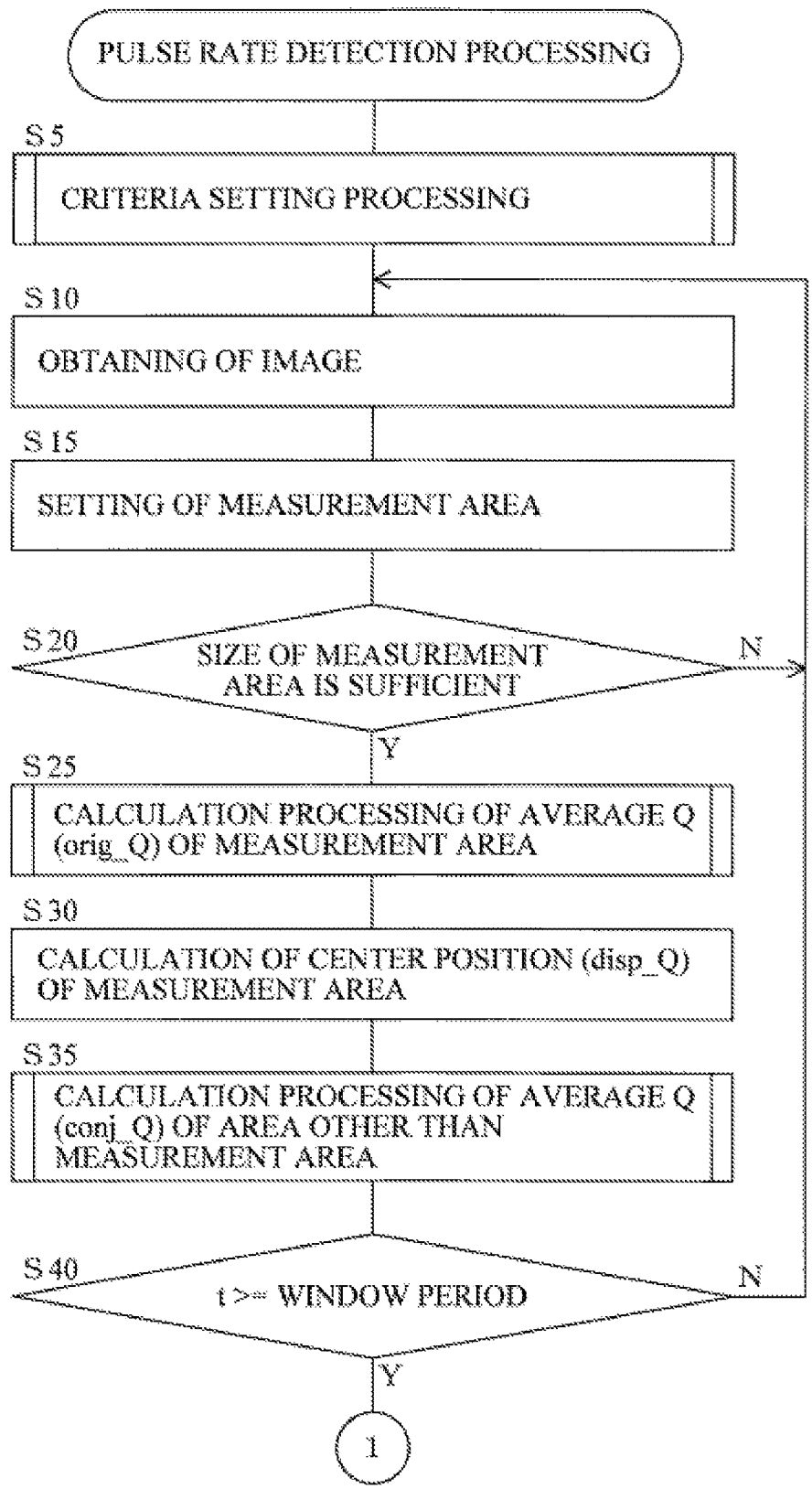
FIG. 2 is a flowchart for describing pulse rate detection processing.
Figure 3A:
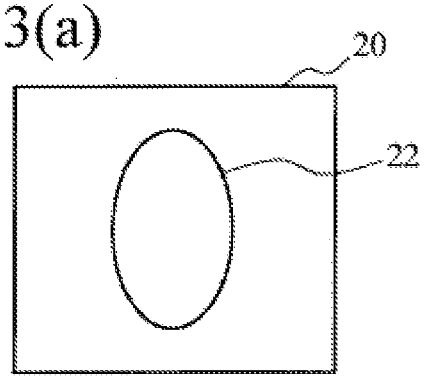
FIG. 3 are diagrams for describing various settings applied to an image.
Figure 3B:
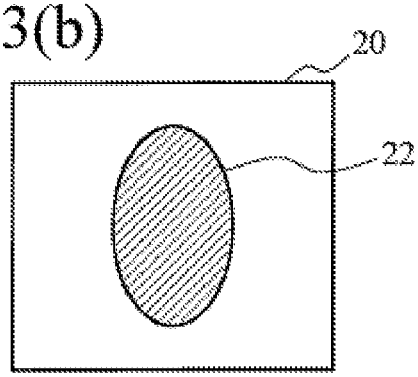
Figure 3C:
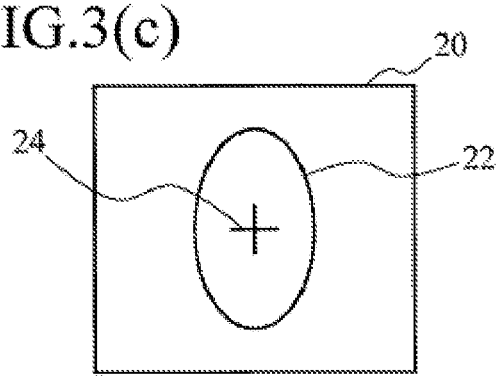
Figure 3D:
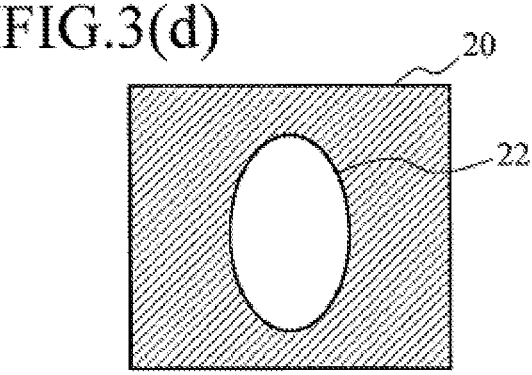

FIG. 2 is a flowchart for describing pulse rate detection processing executed by the pulse rate detection device 1.

The following processing is executed by the CPU 2 in the pulse rate detection device 1 in accordance with the pulse rate detection program stored in the storage unit 10.

First, the pulse rate detection device 1 executes criteria setting processing for setting various criteria for evaluating reliability of the detected pulse rate, evaluating a degree of disturbance, and the like. (Step 5).

Next, the pulse rate detection device 1 obtains a moving image (frame image), captured by the camera 8, by being stored in the RAM 4 (Step 10).

Thus, the pulse rate detection device 1 includes a moving image obtaining means configured to obtain the moving image captured by photographing the body surface of the subject.

Then, the pulse rate detection device 1 sets a measurement area in the obtained moving image to be stored in the RAM 4 (Step 15).

As illustrated in FIG. 3(*a*), the pulse rate detection device 1 detects a face of the subject 11 in the image 20 by a known technique, and sets a measurement area 22 for the face.

Returning to FIG. 2, after setting the measurement area 22, the pulse rate detection device 1 determines whether or not a size of the measurement area 22 is sufficient (Step 20).

If the size of the measurement area 22 is not sufficient (Step 20; N), the pulse rate detection device 1 returns to Step 10 to obtain an (next) image and sets the measurement area 22 thereto. Alternatively, the pulse rate detection device 1 may return to Step 15 to reset the measurement area 22 to the same image.

On the other hand, if the size of the measurement area 22 is sufficient (Step 20; Y), the pulse rate detection device 1 executes calculation processing of an average Q (orig_Q) of the measurement area 22 (Step 25).

This is processing of averaging a Q value of the measurement area 22 portion, i.e., the hatched area illustrated in FIG. 3(*b*), and later detects a pulse rate from a temporal change of the Q value concerned.

Note that orig_Q is an abbreviation for the average Q of the measurement area 22, and, hereinafter, the abbreviation is written in parentheses as required.

Returning to FIG. 2, next, the pulse rate detection device 1 calculates a center position (disp_Q) of the measurement area 22 (Step 30).

As illustrated in FIG. 3(*c*), this is processing of calculating a position of the center 24 of the measurement area 22 to be later used when evaluating a movement disturbance due to a movement of the face.

In for more details, for example, when the face of the subject 11 moves during driving a vehicle, the movement thereof is a disturbance factor (movement disturbance) that reduces detecting accuracy of the pulse rate. Therefore, it is detected on the basis of the movement of the center 24.

As described below, when the peak frequency of the movement of the center 24 in the frequency domain and a pulse rate are closer to each other than a predetermined amount, the pulse rate detection device 1 determines that the reliability of the pulse rate is low due to the movement disturbance and therefore reduces the reliability of the pulse rate.

Thus, the pulse rate detection device 1 includes a reducing means configured to reduce the reliability of the pulse rate if the disturbance peak in the frequency domain of the disturbance factor that reduces the accuracy of the pulse rate is equal to or closer than the predetermined amount to the pulse rate peak.

Accordingly, the disturbance factor concerned is due to the movement of the body surface, and the reducing means reduces the reliability of the moving image if the movement peak in the frequency domain of the movement of the body surface is equal to or closer than the predetermined amount to the pulse rate peak.

Returning to FIG. 2, next, the pulse rate detection device 1 executes calculation processing of the average Q (conj_Q) of the area other than the measurement area 22 (Step 35).

This is processing of averaging the Q value of a portion other than measurement area 22, i.e., the hatched background area other than the measurement area 22 illustrated FIG. 3(*d*) to be later used when evaluating the light disturbance.

In for more details, for example, the state of the light illuminating the face of the subject 11 changes with time during running the vehicle, the change thereof is a disturbance factor (light disturbance) that reduces the detection accuracy of the pulse rate.

In order to know the change in the state of the light illuminating the face, it is necessary to know the change when it does not include the change due to the pulse, but since it appears in an area other than the measurement area 22, which is the background of the face, it is detected by conj_Q.

As described below, when the peak frequency of the conj_Q in the frequency domain and a pulse rate are equal to or closer to each other than a predetermined amount, the pulse rate detection device 1 determines that the reliability of the pulse rate is low due to the light disturbance and therefore reduces the reliability of the pulse rate.

Accordingly, the disturbance factor concerned is due to the variation of light illuminating the body surface, and the reducing means reduces the reliability of the moving image if the light peak in the frequency domain of the variation of light is equal to or closer than the predetermined amount to the pulse rate peak.

Returning to FIG. 2, after executing the above processing, the pulse rate detection device 1 determines whether or not the time elapsed from the start of the obtaining of the image has passed a window period for executing the FFT (Step 40).

If the window period has not passed (Step 40; N), the pulse rate detection device 1 returns to Step 10 to executes the same processing with respect to the next image.

In the present embodiment, the window period is set to 10 seconds, and the above-mentioned processing is executed for images recorded in time series with a moving image for 10 seconds.

Thus, since the images for 10 seconds are prepared in Steps 10 to 40, these images can be converted into the frequency domain by being integrated in the time direction by means of the FFT algorithm.

In more detail, orig_Q, disp_Q, and conj_Q for 10 seconds can be transformed by the FFT, thereby obtaining the frequency components of the pulse rate, the movement disturbance, and the light disturbance can be obtained, respectively.

Figure 4:
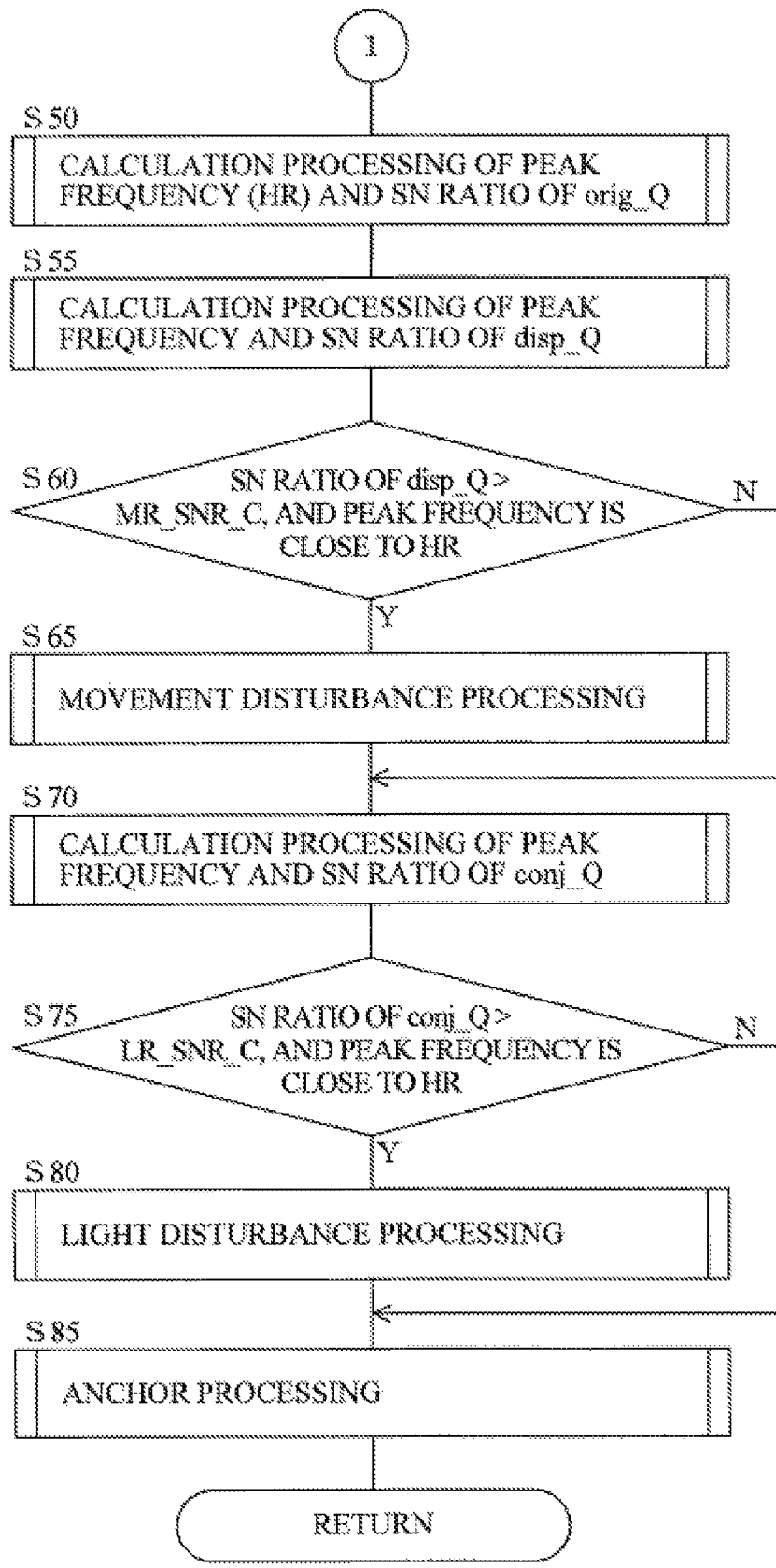
FIG. 4 is flowchart for describing pulse rate detection processing.

FIG. 4 is continued from FIG. 2.

When the window period has elapsed (Step 40; Y), the pulse rate detection device 1 executes calculation processing of a peak frequency (HR) and an SN ratio of the orig_Q (Step 50).

The HR represents the pulse rate of the subject 11, and the SN ratio of the pulse rate signal by the FFT is a basis of the reliability evaluation of the detected pulse rate.

Next, the pulse rate detection device 1 executes calculation processing of a peak frequency and an SN ratio of the disp_Q (Step 55). This is processing of detecting the movement disturbance.

Next, the pulse rate detection device 1 determines whether or not the SN ratio of the disp_Q is greater than the MR_SNR_C and whether or not the peak frequency of the disp_Q (i.e., the peak frequency of the movement disturbance) is close to the HR (Step 60).

The MR_SNR_C used herein is a criteria value of the SN ratio of the movement disturbance, and is set in the criteria setting processing in Step 5 to describe below.

Then, if the SN ratio of disp_Q is greater than the MR_SNR_C and the peak frequency of the disp_Q is close to the HR (Step 60; Y), the pulse rate detection device 1 determines that there is a movement disturbance, and executes movement disturbance processing (Step 65).

On the other hand, if the conditions of Step 60 are not satisfied (Step 60; N), or after executing the processing in Step 65, the pulse rate detection device 1 executes calculation processing of a peak frequency and an SN ratio of the conj_Q (Step 70). This is processing of detecting the light disturbance.

Next, the pulse rate detection device 1 determines whether or not the SN ratio of the conj_Q is greater than the LR_SNR_C and whether or not the peak frequency of the conj_Q (i.e., the peak frequency of the light disturbance) is close to the HR (Step 75).

The LR_SNR_C used herein is a criteria value of the SN ratio of the light disturbance, and is set in the criteria setting processing in Step 5 to describe below.

Then, if the SN ratio of conj_Q is greater than the LR_SNR_C and the peak frequency of the conj_Q is close to the HR (Step 75; Y), the pulse rate detection device 1 determines that there is a light disturbance, and executes light disturbance processing (Step 80).

On the other hand, if the conditions of Step 75 is not satisfied (Step 75; N), or after executing the processing in Step 80, the pulse rate detection device 1 executes display processing of the pulse rate based on the reliability by anchor processing (Step 85).

Hereinafter, each of the above-mentioned processing will now be described using a flowchart.

Figure 5:
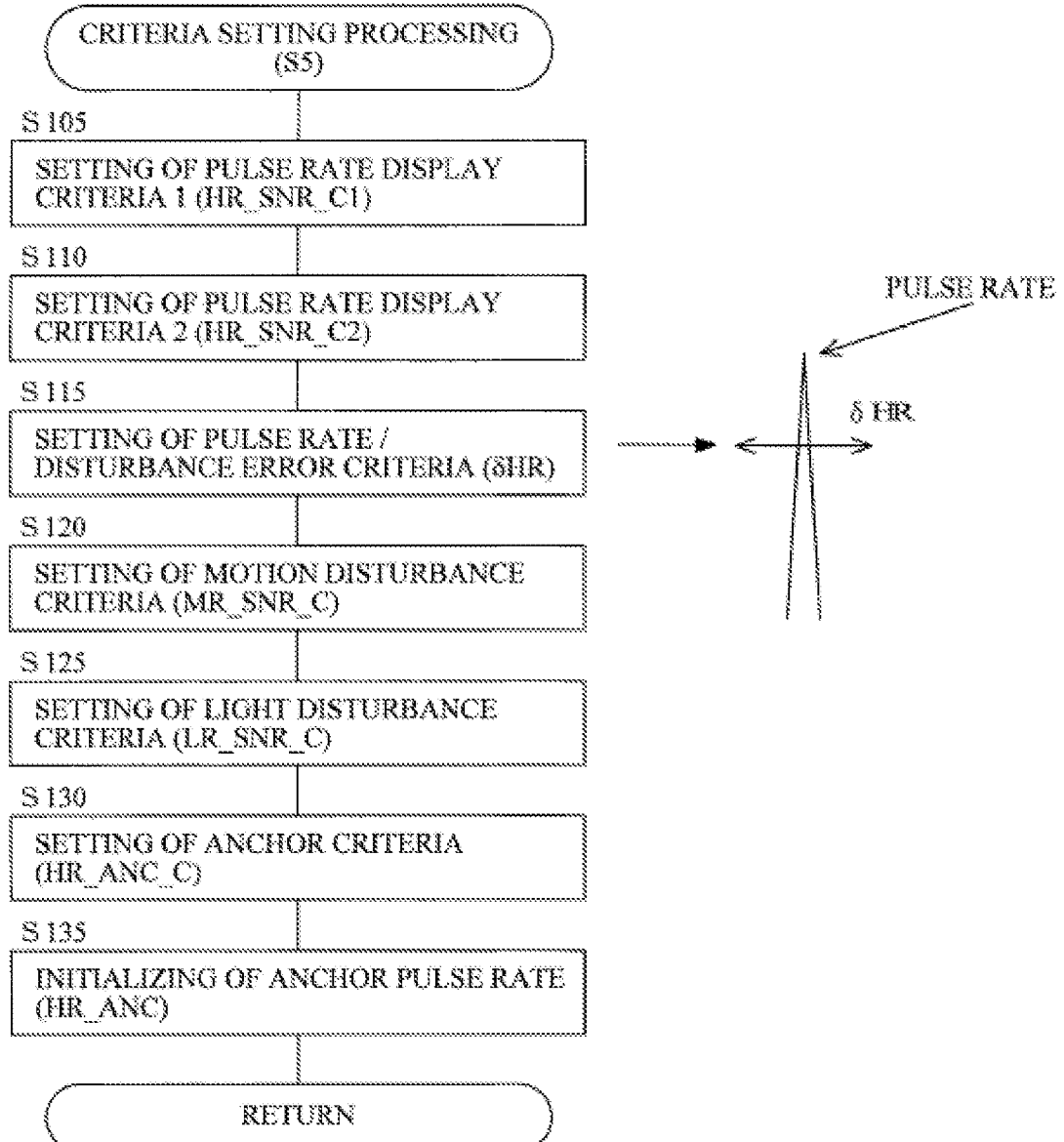
FIG. 5 is a flowchart for describing criteria setting processing.

FIG. 5 is a flowchart for describing the criteria setting processing (Step 5 illustrated in FIG. 2).

First, the pulse rate detection device 1 is set the pulse rate display criteria 1 (HR_SNR_C1) by being stored in the RAM 4 (Step 105).

This is first criteria for evaluating the reliability, and if the reliability of the pulse rate is equal to or greater than the HR_SNR_C1, the pulse rate detection device 1 outputs the pulse rate as having high reliability.

Thus, the pulse rate detection device 1 includes a reliability obtaining means configured to obtain reliability of the pulse rate, and an output means configured to output the pulse rate concerned if the reliability thereof is equal to or greater than the predetermined reliable criteria.

Next, the pulse rate detection device 1 sets the pulse rate display criteria 2 (HR_SNR_C2) by being stored in the RAM 4 (Step 110).

This is second criteria for evaluating the reliability and has a value smaller than that of the HR_SNR_C1.

Even if the reliability of the pulse rate does not satisfy the HR_SNR_C1 but satisfies the HR_SNR_C2, the pulse rate detection device 1 displays the pulse rate, on condition that the detected pulse rate is close to an immediate past pulse rate.

This is to relieve the case where the reliability is slightly inferior by using the fact that the pulse rate does not rapidly change, and thereby the pulse rate detection device 1 can increase the effective detection period of the pulse rate.

Thus, the output means included in the pulse rate detection device 1 outputs the pulse rate obtained if the reliability of the pulse rate is equal to or greater than the predetermined reliable criteria (i.e., the pulse rate display criteria 1) and if the reliability thereof is less than the reliable criteria concerned and the change of the pulse rate is within the predetermined appropriate range.

In this case, the change of the pulse rate is a difference between the pulse rate detected this time and the immediate past pulse rate, and the output means outputs the pulse rate as being within the appropriate range if the difference therebetween is equal to or less than the predetermined criteria (equal to or less than the below-mentioned anchor criteria).

Next, the pulse rate detection device 1 sets a pulse rate/disturbance error criteria (δHR) by being stored in the RAM 4 (Step 115).

In the present embodiment, the δHR is set to 5 bpm, and the presence of the disturbance is determined whether or not it is within a range of the HR ±5 bpm.

For example, if the peak of the movement disturbance and/or the light disturbance is within a range of the HR±5 bpm, the pulse rate detection device 1 determines that there is the disturbance on condition that the conditions with regard to the SN ratio of these disturbance factors itself are satisfied (Steps 60 and 75).

Next, the pulse rate detection device 1 sets the motion disturbance criteria (MR_SNR_C) by being stored in the RAM 4 (Step 120), and further sets the light disturbance criteria (LR_SNR_C) by being stored in the RAM 4 (Step 125).

This is the criteria of the SN ratio of the disturbance factor itself used in Steps 60 and 75.

Next, the pulse rate detection device 1 sets the anchor criteria (HR_ANC_C) by being stored in the RAM 4 (Step 130), and further initializes an appropriate initial value of the anchor pulse rate (HR_ANC) by being stored in the RAM 4 (Step 135).

The anchor pulse rate is a variable that contains an immediate past pulse rate, and the anchor criteria is criteria for determining a closeness between the detected pulse rate and the immediate past pulse rate. That is, the pulse rate detection device 1 determines the newest pulse rate detected this time is within the appropriate range if the difference between the latest pulse rate and the immediate past pulse rate is equal to or less than the anchor criteria.

Figure 6:
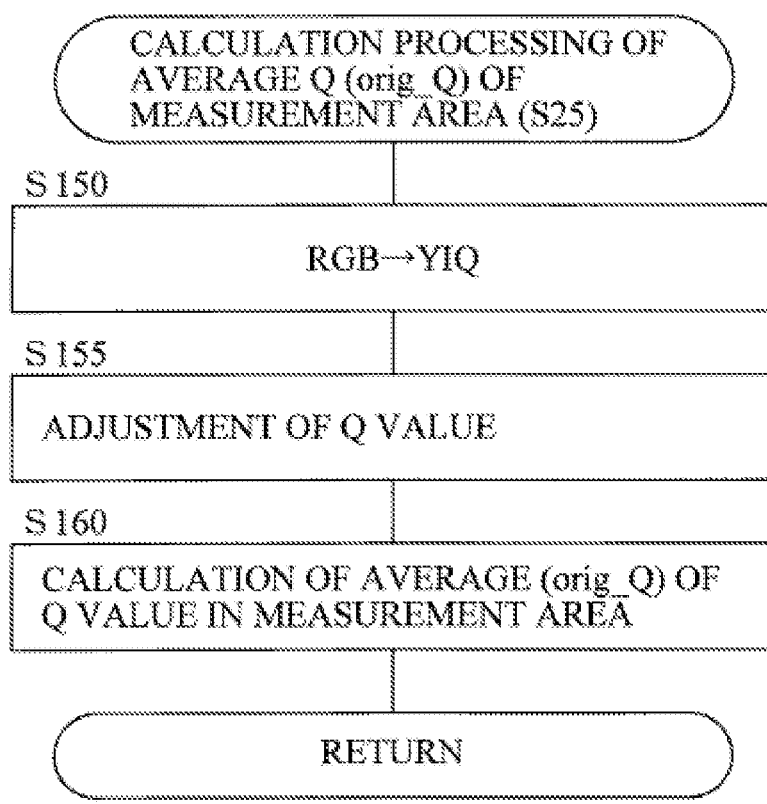
FIG. 6 is a flowchart for describing calculation processing of an average Q of a measurement area.

FIG. 6 is a flowchart for describing the calculation processing of the average Q (orig_Q) of the measurement area 22 (Step 25 illustrated in FIG. 2).

First, the pulse rate detection device 1 converts a color space of the image 20 stored in the RAM 4 from RGB to YIQ, and stores the image 20 based on the converted Q value in the RAM 4 (Step 150). The image 20 based on the Q value is used in the subsequent processing. The reason why the image 20 based on the Q value is created in this way is because the Q value is suitable for detection of the pulse rate.

Next, the pulse rate detection device 1 adjusts (calibrates) the Q value of each pixel as a countermeasure against influence due to characteristics of the camera 8 (Step 155). This is to compensate for variations in a performance of the pixel that composes a frame image by scaling the value of each pixel.

Next, the pulse rate detection device 1 calculates the mean (orig_Q) by averaging the Q value of the pixels in the measurement area 22 to be stored in the RAM 4 (Step 160).

The pulse rate detection device 1 then returns to a main routine.

Figure 7:
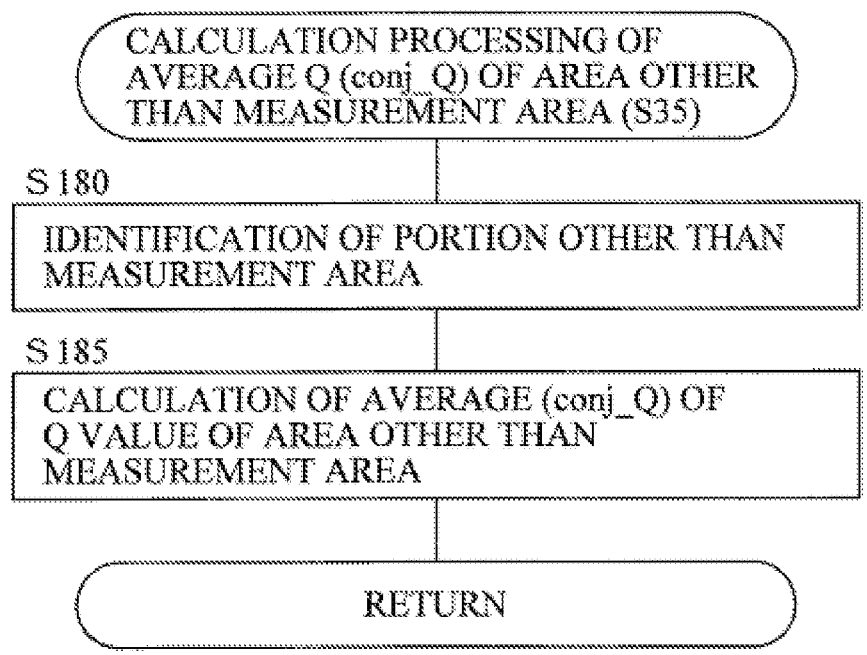
FIG. 7 is a flowchart for describing the calculation processing of the average Q of areas other than a measurement area.

FIG. 7 is a flowchart for describing the calculation processing of the average Q (conj_Q) in the area other than the measurement area 22 (Step 35 illustrated in FIG. 2).

First, the pulse rate detection device 1 identifies portions other than the measurement area 22, in the image 20 stored in the RAM 4, from which the measurement area 22 is excepted (Step 180).

Then, the pulse rate detection device 1 calculates the mean (conj_Q) by averaging the Q value of the pixels in the identified portion other than the measurement area 22 to be stored in the RAM 4 (Step 185).

The pulse rate detection device 1 then returns to the main routine.

FIG. 8 is a flowchart for describing the calculation processing of the peak frequency (HR) and the SN ratio of the orig_Q (Step 50 of FIG. 4).

First, the pulse rate detection device 1 reads the orig_Q for 10 seconds stored in the RAM 4, and generates FFT_HR by Fourier-transforming with the FFT and stores the FFT_HR in the RAM 4 (Step 205).

The FFT_HR is data obtained by converting the orig_Q from the time domain to the frequency domain (when drawn on a graph, as illustrated in FIG. 1($b$), for example), and the maximum peak (pulse rate signal) based on the pulse rate appears around 60 bpm.

Therefore, the pulse rate detection device 1 identifies the frequency (HR) of the maximum peak of the FFT_HR to be stored in the RAM 4 (Step 210). This corresponds to the pulse rate of the subject 11.

Thus, the pulse rate detection device 1 includes a pulse rate obtaining means configured to obtain the subject's pulse rate on the basis of the change in the pixel values (e.g., Q value, infrared brightness) of the body surface in the moving image, and the pulse rate obtaining means concerned obtains the pulse rate from the pulse rate peak in the frequency domain of the moving image.

Next, the pulse rate detection device 1 generates a mask (HR_M1) of the maximum peak frequency ±5 bpm to be stored in the RAM 4 (Step 215).

The HR_M1 is data that is 1 in a case of the range of HR±5 bpm, and is 0 in a case of the other range. The HR_M1 is used together with the HR_M2 described later to extract a portion of a pulse rate signal from an FFT waveform when the SN ratio is calculated later.

Next, the pulse rate detection device 1 generates a mask (HR_M2) of harmonic ±5 bpm of the maximum peak to be stored in the RAM 4 (Step 220).

This is because a second harmonic of the pulse rate also appears in the frequency domain of the FFT performed by the pulse rate detection device 1, and therefore the mask used therefor is also created.

Next, the pulse rate detection device 1 generates one mask (HR_M) by adding the HR_M1 and the HR_M2 stored in the RAM 4 to each other, and stores the generated mask in the RAM 4 (Step 225).

The HR_M is a mask that is 1 at a portion of ±5 bpm centering on the HR and ±5 bpm centering on the second harmonic of HR, and is 0 in the other portions.

Next, the pulse rate detection device 1 creates a disturbance mask of the HR_M (HRN_M=1−HR_M) to be stored in the RAM 4 (Step 230).

The HRN_M is an inversion 1 and 0 of the HR_M, and is 0 at a portion of ±5 bpm centering on the HR and ±5 bpm centering on the second harmonic of the HR, and is 1 in the other portion.

Next, the pulse rate detection device 1 normalizes the FFT_HR stored in the RAM 4 and stores the normalized data (FFT_HRn) in the RAM 4 (Step 235).

The pulse rate detection device 1 calculates this normalization by (FFT_HRn=FFT_HR/maximum value of FFT_HR).

Next, the pulse rate detection device 1 calculates the num by substituting the FFT_HRn stored in the RAM 4 into the equation of num illustrated in FIG. 8, and stores the result thereof in the RAM 4 (Step 240).

The pulse rate detection device 1 analyzes by means of the FFT the moving image data accumulated for 10 seconds, and this is repeated with respect to the latest data for every second. Therefore, the pulse rate detection device 1 generates latest values of FFT_HRn, HR_M, and HRN_M in time series for every second.

Therefore, in the calculation of the num or the following den, in order to equalize variations of the data, i of these values are added.

The equation of the num is an inner product of a vector having a component of the square of FFT_HRn (i) and the HR_M (i) which is a vector having a component of 0, 1 of the mask, and obtains a value proportional to power of the signal in the portion of ±5 bpm centered on the HR and the portion of ±5 bpm centered on the second harmonic of the HR. That is, the pulse rate detection device 1 extracts the portion corresponding to the pulse rate signal from the FFT_HRn(i), and calculates a value proportional to the power thereof (since it is normalized).

Next, the pulse rate detection device 1 similarly calculates the den by substituting the FFT_HRn stored in the RAM 4 into the equation of den illustrated in FIG. 8, and stores the result thereof in the RAM 4 (Step 245).

Since the HRN_M(i) is obtained by inverting the HR_M (i), a value obtained by the den is proportional to the power of the signal at the portion except the portion of ±5 bpm centering on the HR and the portion of ±5 bpm centering on the second harmonic of the HR. That is, the pulse rate detection device 1 extracts the portion not corresponding to the pulse rate signal from the FFT_HRn(i), and calculates a value proportional to the power thereof (since it is normalized).

Next, the pulse rate detection device 1 generates HR_SNR, which is a bases of the reliability of the pulse wave, by substituting respectively the num and the den which have been stored in the RAM 4 into the numerator and the denominator in the equation of the HR_SNR illustrated in FIG. 8, and stores the generated HR_SNR in the RAM 4 (Step 250).

The pulse rate detection device 1 then returns to the main routine.

The equation of HR_SNR is a general equation expressing the SN ratio, and expresses a degree of the signal with respect to the noise by dividing the num by the den.

The pulse rate detection device 1 uses the HR_SNR as the initial value of the reliability of the pulse rate, and reduces this depending on the influence of the disturbance factor or controls the display of the pulse rate.

Thus, the reliability obtaining means included in the pulse rate detection device 1 obtains the reliability on the basis of the SN ratio of the pulse rate.

Figure 9:
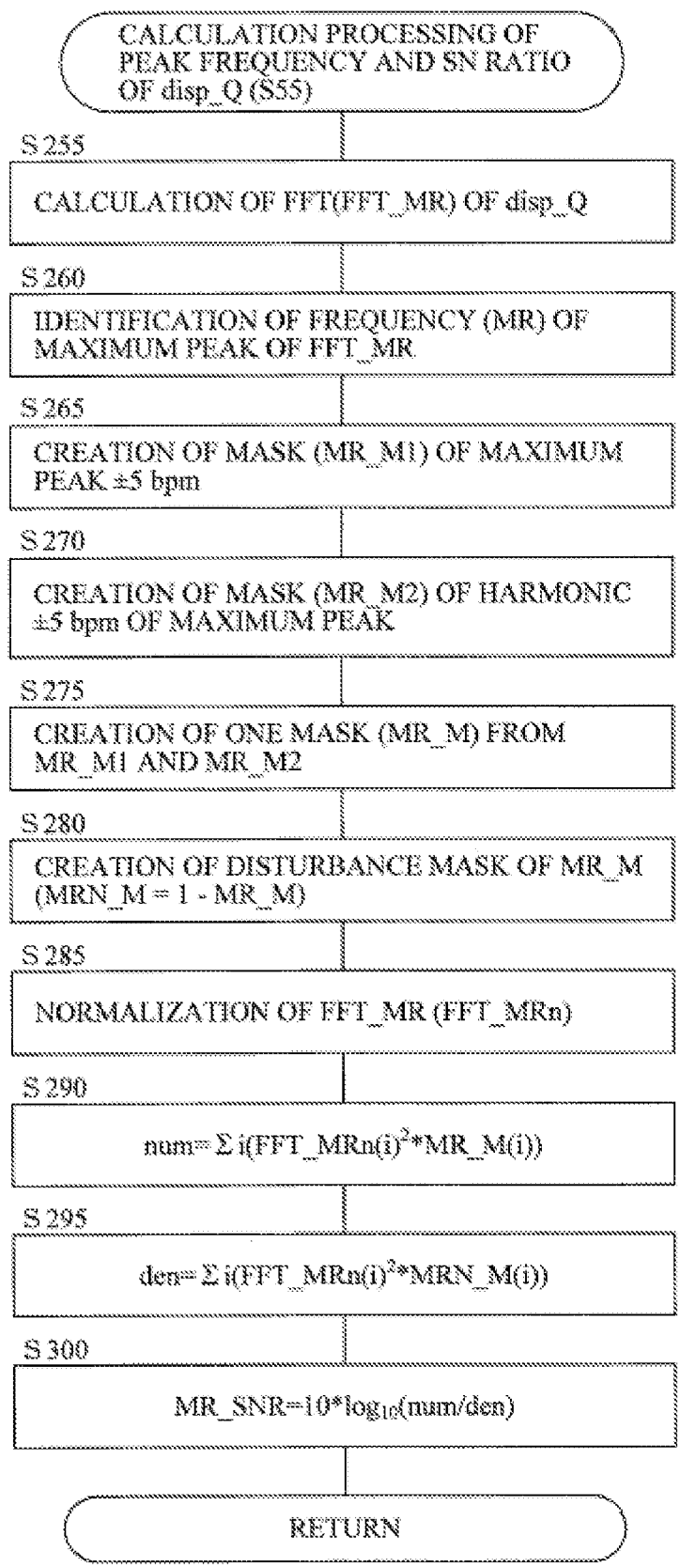
FIG. 9 is a flowchart for describing calculation processing of a peak frequency and an SN ratio of disp_Q.

FIG. 9 is a flowchart for describing calculation processing of the peak frequency (MR) and the SN ratio of the disp_Q (Step 55 illustrated in FIG. 4).

The procedure of processing is the same as that of the case of the orig_Q, and the description of common portions are simplified.

First, the disp_Q for 10 seconds which has been stored in the RAM 4 is read and then is Fourier-transformed by means of the FFT. Thereby, the pulse rate detection device 1 generates FFT_MR which is an FFT value of the disp_Q, to be stored in the RAM 4 (Step 255).

The FFT_MR is a frequency component of the movement disturbance, and the pulse rate detection device 1 identifies the frequency (MR) of the maximum peak of the FFT_MR to be stored in the RAM 4 (Step 260).

Next, the pulse rate detection device 1 generates a mask (MR_M1) of the maximum peak frequency ±5 bpm to be stored in the RAM 4 (Step 265).

Next, the pulse rate detection device 1 generates a mask (MR_M2) of harmonic ±5 bpm of the maximum peak to be stored in the RAM 4 (Step 270).

Next, the pulse rate detection device 1 generates one mask (MR_M) by adding the MR_M1 and the MR_M2 stored in the RAM 4 to each other, and stores the generated mask in the RAM 4 (Step 275).

Next, the pulse rate detection device 1 creates a disturbance mask of the MR_M (MRN_M=1−MR_M) to be stored in the RAM 4 (Step 280).

Next, the pulse rate detection device 1 normalizes the FFT_MR stored in the RAM 4 and stores the normalized data (FFT_MRn) in the RAM 4 (Step 285).

The pulse rate detection device 1 calculates this normalization by (FFT_MRn=FFT_MR/maximum value of FFT_MR).

Next, the pulse rate detection device 1 calculates the num by substituting the FFT_MRn stored in the RAM 4 into the equation of num illustrated in FIG. 9, and stores the result thereof in the RAM 4 (Step 290).

Next, the pulse rate detection device 1 similarly calculates the den by substituting the FFT_MRn stored in the RAM 4 into the equation of den illustrated in FIG. 9, and stores the result thereof in the RAM 4 (Step 295).

Next, the pulse rate detection device 1 generates MR_SNR, based on the movement disturbance, by substituting the num and the den which have been stored in the RAM 4 into the equation of the MR_SNR illustrated in FIG. 9, and stores the generated MR_SNR in the RAM 4 (Step 300).

The pulse rate detection device 1 then returns to the main routine.

This MR_SNR is used as the SN ratio of the disp_Q in Step 60 illustrated in FIG. 4.

Figure 10:
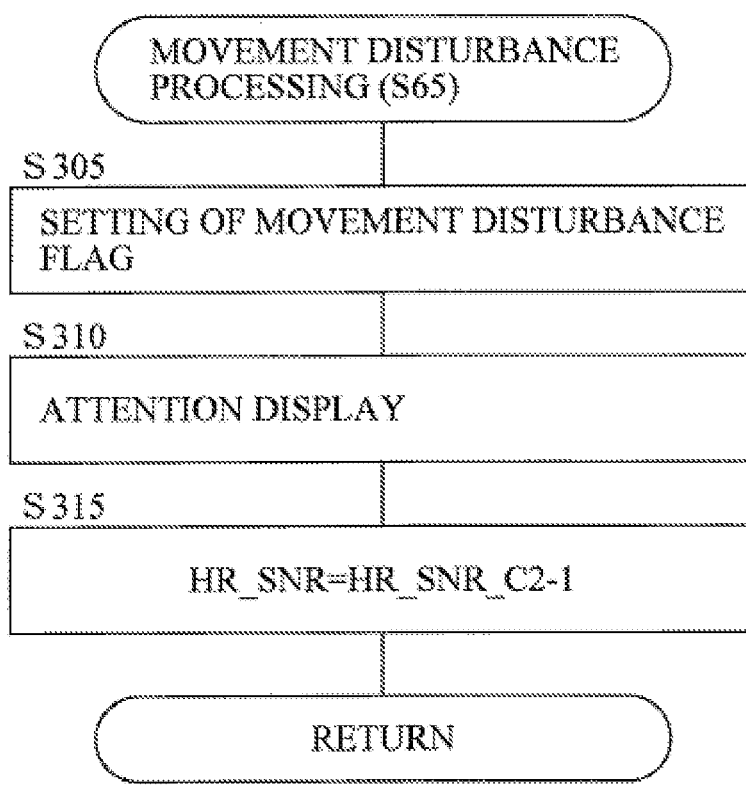
FIG. 10 is a flowchart for describing movement disturbance processing.

FIG. 10 is a flowchart for describing the movement disturbance processing (Step 65 illustrated in FIG. 4).

The pulse rate detection device 1 sets 1 to a movement disturbance flag and thereby the movement disturbance flag is set on (Step 305).

The pulse rate detection device 1 stores the movement disturbance flag in the RAM 4, and sets 0 to the movement disturbance flag if there is no movement disturbance and sets 1 to the movement disturbance flag so as to be set on if there is a movement disturbance.

Next, the pulse rate detection device 1 displays an attention "Attention: Movement Disturbance" or the like on the display unit 5 (FIG. 1), indicating that a movement disturbance has occurred (Step 310).

Furthermore, the pulse rate detection device 1 updates the HR_SNR to HR_SNR_C2−1 to be stored in the RAM 4 (Step 315).

The pulse rate detection device 1 then returns to the main routine.

Thus, since, if there is a movement disturbance, the reliability of a pulse rate is low, the pulse rate detection device 1 reduces the reliability from the HR_SNR to a value that is only one smaller than the HR_SNR_C2, and does not display the pulse rate in the subsequent anchor processing.

Figure 11:
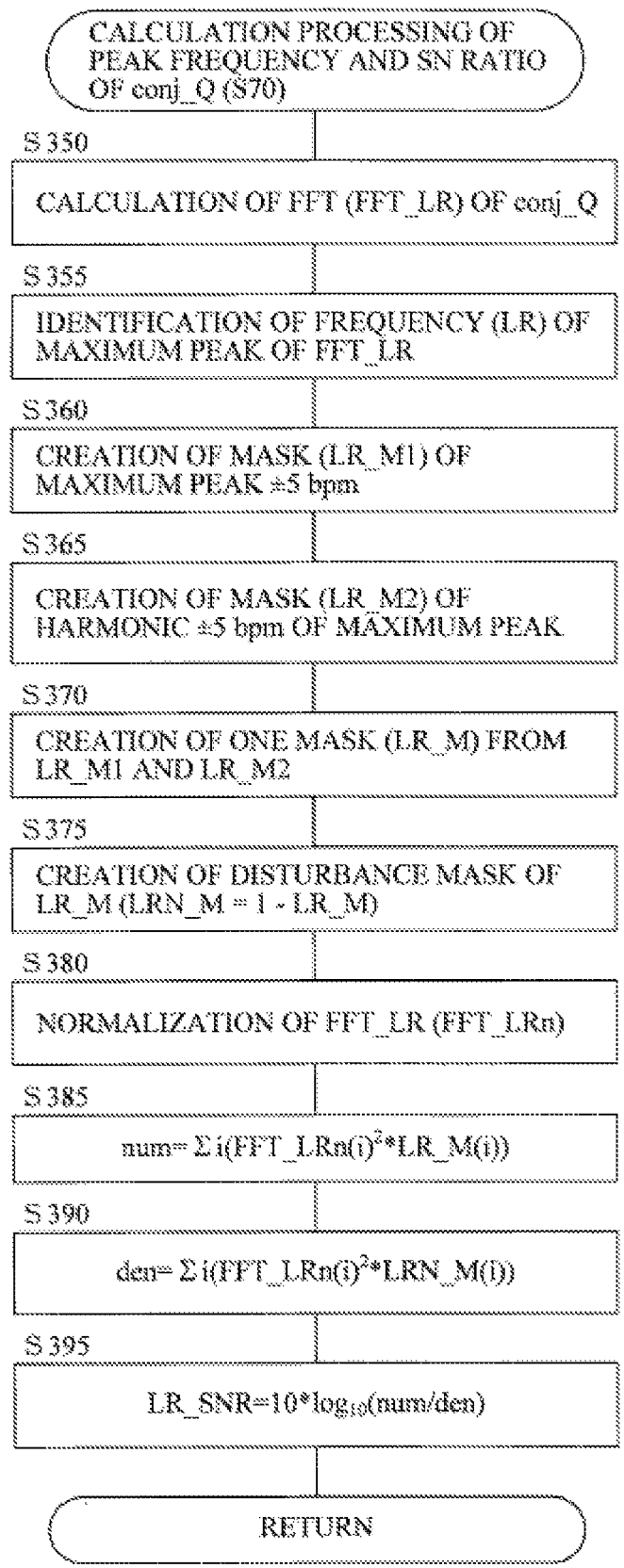
FIG. 11 is a flowchart for describing calculation processing of a peak frequency and an SN ratio of conj_Q.

FIG. 11 is a flowchart for describing calculation processing of the peak frequency (LR) and the SN ratio of the conj_Q (Step 70 illustrated in FIG. 4).

The procedure of processing is the same as that of the case of the orig_Q, and the description of common portions are simplified.

First, the conj_Q for 10 seconds which has been stored in the RAM 4 is read and then is Fourier-transformed by means of the FFT. Thereby, the pulse rate detection device 1 generates FFT_LR which is an FFT value of the conj_Q, to be stored in the RAM 4 (Step 350).

The FFT_LR is a frequency component of the light disturbance, and the pulse rate detection device 1 identifies the frequency (LR) of the maximum peak of the FFT_LR to be stored in the RAM 4 (Step 355).

Next, the pulse rate detection device 1 generates a mask (LR_M1) of the maximum peak frequency ±5 bpm to be stored in the RAM 4 (Step 360).

Next, the pulse rate detection device 1 generates a mask (LR_M2) of harmonic ±5 bpm of the maximum peak to be stored in the RAM 4 (Step 365).

Next, the pulse rate detection device 1 generates one mask (LR_M) by adding the LR_M1 and the LR_M2 stored in the RAM 4 to each other, and stores the generated mask in the RAM 4 (Step 370).

Next, the pulse rate detection device 1 creates a disturbance mask of the LR_M (LRN_M=1−LR_M) to be stored in the RAM 4 (Step 375).

Next, the pulse rate detection device 1 normalizes the FFT_LR stored in the RAM 4 and stores the normalized data (FFT_LRn) in the RAM 4 (Step 380).

The pulse rate detection device 1 calculates this normalization by (FFT_LRn=FFT_LR/maximum value of FFT_LR).

Next, the pulse rate detection device 1 calculates the num by substituting the FFT_LRn stored in the RAM 4 into the equation of num illustrated in FIG. 11, and stores the result thereof in the RAM 4 (Step 385).

Next, the pulse rate detection device 1 similarly calculates the den by substituting the FFT_LRn stored in the RAM 4 into the equation of den illustrated in FIG. 11, and stores the result thereof in the RAM 4 (Step 390).

Next, the pulse rate detection device 1 generates LR_SNR, based on the light disturbance, by substituting the num and the den which have been stored in the RAM 4 into the equation of the LR_SNR illustrated in FIG. 11, and stores the generated LR_SNR in the RAM 4 (Step 395).

The pulse rate detection device 1 then returns to the main routine.

This LR_SNR is used as the SN ratio of the conj_Q in Step 75 illustrated in FIG. 4.

Figure 12:
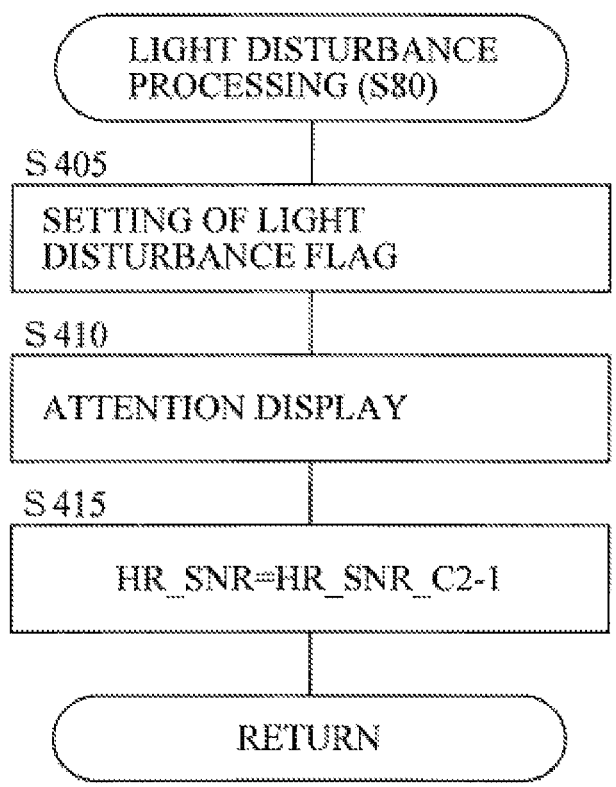
FIG. 12 is a flowchart for describing light disturbance processing.

FIG. 12 is a flowchart for describing the light disturbance processing (Step 80 illustrated in FIG. 4).

The pulse rate detection device 1 sets 1 to a light disturbance flag which has been stored in the RAM 4 and thereby the light disturbance flag is set on (Step 405).

The pulse rate detection device 1 stores the light disturbance flag in the RAM 4, and sets 0 to the light disturbance flag if there is no light disturbance and sets 1 to the light disturbance flag so as to be set on if there is a light disturbance.

Next, the pulse rate detection device 1 displays an attention "Attention: Light Disturbance" or the like on the display unit 5 (FIG. 1), indicating that a light disturbance has occurred (Step 410).

Furthermore, the pulse rate detection device 1 updates the HR_SNR to HR_SNR_C2−1 to be stored in the RAM 4 (Step 415).

The pulse rate detection device 1 then returns to the main routine.

Thus, since, if there is a light disturbance, the reliability of a pulse rate is low, the pulse rate detection device 1 reduces the reliability from the HR_SNR to a value that is only one smaller than the HR_SNR_C2, and does not display the pulse rate in the subsequent anchor processing.

Figure 13:
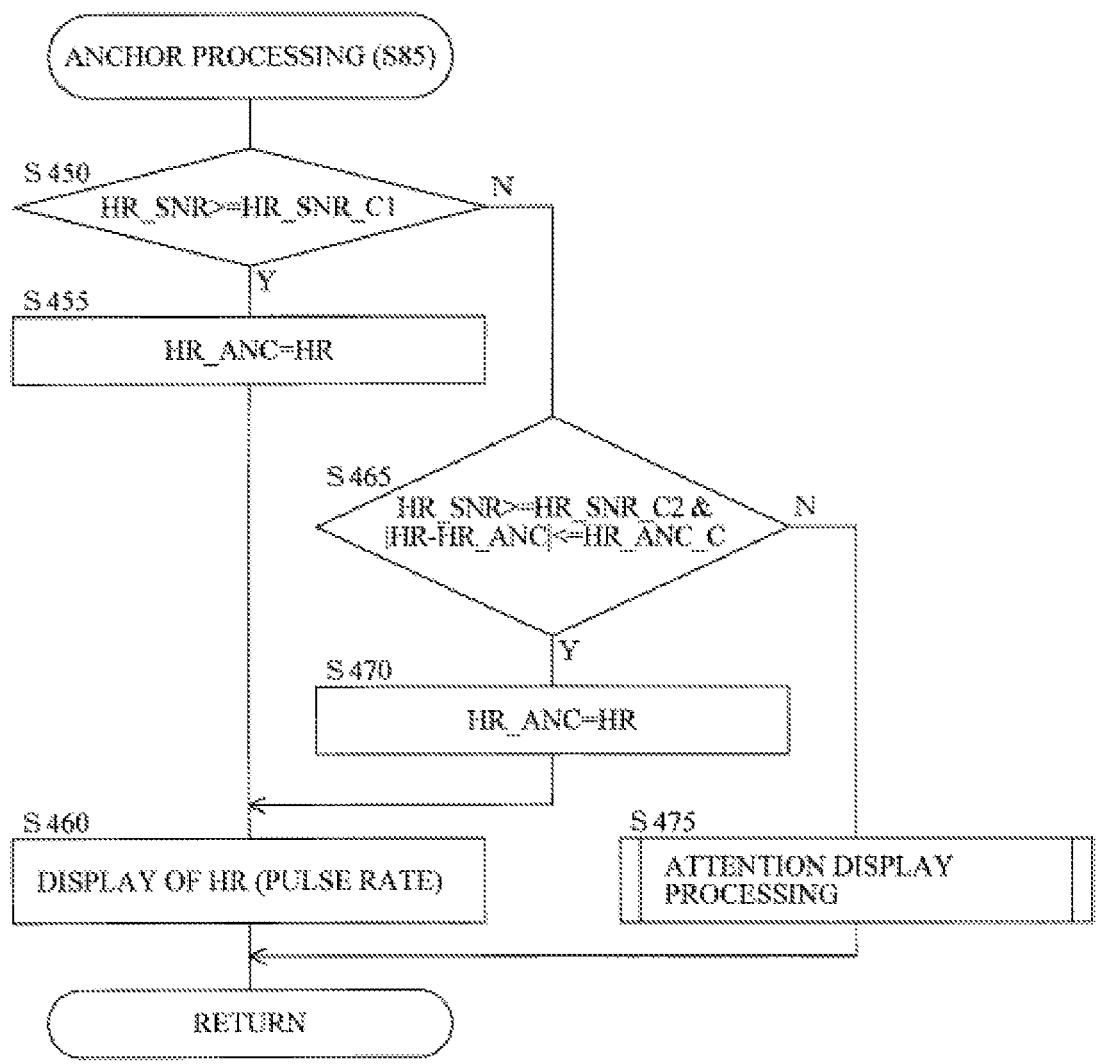
FIG. 13 is a flowchart for describing anchor processing.

FIG. 13 is a flowchart for describing the anchor processing (Step 85 illustrated in FIG. 4).

The anchor processing is processing of controlling the display of the pulse rate in accordance with the reliability of the pulse rate.

First, the pulse rate detection device 1 reads the HR_SNR (reliability) and the HR_SNR_C1 (pulse rate display criteria 1) from the RAM 4, and compares a magnitude relationship therebetween (Step 450).

If the HR_SNR (reliability) is equal to or greater than the HR_SNR_C1 (pulse rate display criteria 1) (Step 450; Y), the pulse rate detection device 1 substitutes the HR (detected pulse rate) to the HR_ANC (anchor pulse rate) to be stored in the RAM 4 (Step 455). This is processing of storing the immediate past pulse rate in the HR_ANC.

The pulse rate detection device 1 then displays the HR (pulse rate) on the display unit 5 (Step 460), and returns to the main routine.

On the other hand, if the HR_SNR (reliability) is less than the HR_SNR_C1 (pulse rate display criteria 1) (Step 450; N), the pulse rate detection device 1 determines whether or not the HR_SNR (reliability) is equal to or greater than the HR_SNR_C2 (pulse rate display criteria 2) and a difference between the HR (detected pulse rate) and the HR_ANC (immediate past pulse rate) is equal to or less than the HR_ANC_C (anchor criteria) (Step 465).

If such conditions are satisfied (Step 465; Y), the pulse rate detection device 1 substitutes the HR (detected pulse rate) to the HR_ANC (anchor pulse rate) to be stored in the RAM 4 (Step 470), displays the HR (detected pulse rate) on the display unit 5 (Step 460), and returns to the main routine.

On the other hand, if at least one of the conditions is not satisfied (Step 465; N), the pulse rate detection device 1 executes the attention display processing (Step 475), and returns to the main routine.

Figure 14:
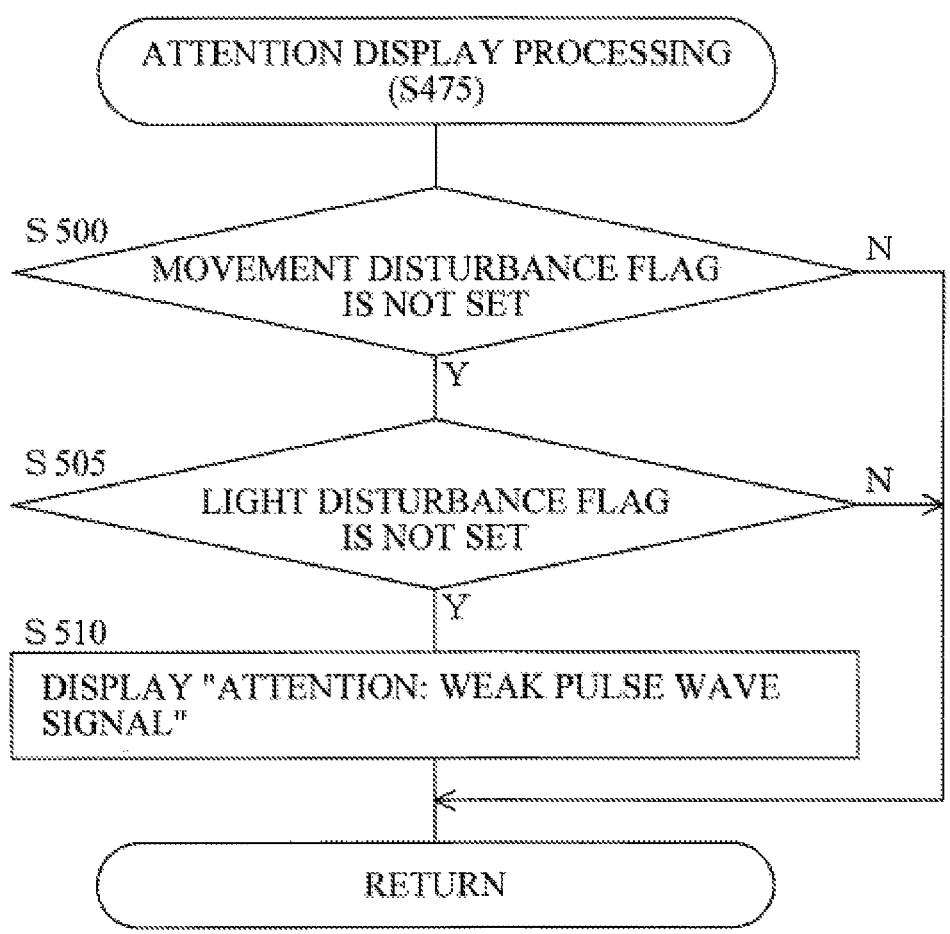
FIG. 14 is a flowchart for describing a procedure of attention display processing.

FIG. 14 is a flowchart for describing a procedure of the attention display processing in Step 475 (FIG. 13).

The pulse rate detection device 1 determines whether or not the movement disturbance flag which has been stored in the RAM 4 is set on (Step 500).

If the movement disturbance flag is set on (Step 500; N), the pulse rate detection device 1 returns to the anchor processing.

On the other hand, if the movement disturbance flag is not set on (Step 500; Y), the pulse rate detection device 1 further determines whether or not the light disturbance flag is set on (Step 505).

If the light disturbance flag is set on (Step 505; N), the pulse rate detection device 1 returns to the anchor processing.

On the other hand, if the light disturbance flag is not set on (Step 505; Y), the pulse rate detection device 1 displays on the display unit 5 "Attention: Weak Pulse Wave Signal" (Step 510), and returns to the anchor processing.

The following effects can be obtained by the embodiment described above.

(1) The reliability of the detected pulse rate can be quantitatively evaluated.

(2) The characteristics of the disturbance are estimated, and thereby it is possible to suppress the movement disturbance and the light disturbance from being mistaken for the pulse.

(3) Since the movement disturbance and the light disturbance are suppressed from being mistaken for the pulse, the reliability of he detected pulse rate can be improved.

(4) Even if the reliability of the detected pulse rate is low to some extent, by being compared with the pulse rate of immediate past (before one second) on the basis of the characteristics of the human body that the pulse rate does not change suddenly, the reliability thereof can be improved, thereby increasing the rate at which the pulse rate can be detected.

(5) The period during which the pulse rate can detected can be determined on the basis of the display of the reliability of the pulse rate.

In the present embodiment, if there is a disturbance, the pulse rate is not displayed by setting the HR_SNR to the HR_SNR_C2-1, but the degree of the disturbance may further be subdivided, and the display of the pulse rate may be controlled according to the degree thereof.

Moreover, in the present embodiment, the display/non-display of the pulse rate is controlled on the basis of the reliability, but various kinds of output forms are possible, such as outputting the pulse rate with the reliability thereof, or outputting it to a control system of a vehicle, for example.

According to this embodiment, the following configurations can be obtained.

(First configuration) A pulse rate detection device comprising: a moving image obtaining means configured to obtain a moving image captured by photographing a body surface of a subject; a pulse rate obtaining means configured to obtain a pulse rate of the subject on the basis of change of a pixel value of the body surface in the moving image; a reliability obtaining means configured to obtain reliability of the obtained pulse rate; and an output means configured to output the obtained pulse rate if the obtained reliability thereof is equal to or greater than predetermined reliable criteria.

(Second configuration) The pulse rate detection device according to first configuration, wherein the pulse rate obtaining means obtains the pulse rate from a pulse rate peak in a frequency domain of the obtained moving image, and the reliability obtaining means obtains the reliability on the basis of an SN ratio of the obtained pulse rate.

(Third configuration) The pulse rate detection device according to second configuration, further comprising a reducing means configured to reduce the reliability if a disturbance peak in the frequency domain of a disturbance factor that reduces accuracy of the obtained pulse rate is equal to or closer than a predetermined amount to the obtained pulse rate peak.

(Fourth configuration) The pulse rate detection device according to third configuration, wherein the disturbance factor is due to a movement of the body surface, and the reducing means reduces the reliability if a movement peak in the frequency domain of the movement of the body surface is equal to or closer than the predetermined amount to the obtained pulse rate peak.

(Fifth configuration) The pulse rate detection device according to third or fourth configuration, wherein the disturbance factor is due to variation of light illuminating the body surface, and the reducing means reduces the reliability if a light peak in the frequency domain of the variation of light is equal to or closer than the predetermined amount to the obtained pulse rate peak.

(Sixth configuration) A pulse rate detection program for causing a computer to realize: a moving image obtaining function for obtaining a moving image captured by photographing a body surface of a subject; a pulse rate obtaining function for obtaining a pulse rate of the subject on the basis of change of a pixel value of the body surface in the moving image; a reliability obtaining function for obtaining reliability of the obtained pulse rate; and an output function for outputting the obtained pulse rate if the obtained reliability thereof is equal to or greater than predetermined reliable criteria.

REFERENCE SIGNS LIST

1 Pulse rate detection device
2 CPU
3 ROM
4 RAM
5 Display unit
6 Input unit
7 Output unit
8 Camera
10 Storage unit
11 Subject
20 Image
22 Measurement area
24 Center

The invention claimed is:

1. A pulse rate detection device comprising:
a moving image obtaining means configured to obtain a moving image captured by photographing a body surface of a subject;
a pulse rate obtaining means configured to obtain a pulse rate of the subject on the basis of change of a pixel value of the body surface in the moving image;
a reliability obtaining means configured to obtain reliability of the obtained pulse rate;
a processor that is configured to determine: (1) if the obtained reliability is equal to or greater than a first predetermined reliable criteria and (2) if the obtained reliability is less than the first predetermined reliable criteria and is equal to or greater than a second predetermined reliable criteria that is less than the first predetermined reliable criteria and that a difference between the obtained pulse rate and an immediate past pulse rate is equal to or less than a predetermined reference; and
an output means configured to output the obtained pulse rate, wherein:
the output means outputs the obtained pulse rate when the processor determines that the obtained reliability is equal to or greater than the first predetermined reliable criteria, or
the output means outputs the obtained pulse rate when the processor determines that the obtained reliability is less than the first predetermined reliable criteria and is equal to or greater than the second predetermined reliable criteria that is less than the first predetermined reliable criteria and the difference between the obtained pulse rate and the immediate past pulse rate is equal to or less than the predetermined reference,
wherein:
the pulse rate obtaining means obtains the pulse rate from a pulse rate peak in a frequency domain of the obtained moving image, and
the reliability obtaining means obtains the reliability on the basis of a signal-to-noise (SN) ratio of the obtained pulse rate.

2. The pulse rate detection device according to claim 1, wherein
the output means outputs an attention display if at least one of the conditions is not satisfied: (1) the obtained reliability is equal to or greater than the second predetermined reliable criteria and (2) the difference between the obtained pulse rate and the immediate past pulse rate is equal to or less than the predetermined reference.

3. The pulse rate detection device according to claim 2, further comprising
a reducing means configured to reduce the reliability if a disturbance peak in the frequency domain of a disturbance factor that reduces accuracy of the obtained pulse rate is equal to or closer than a predetermined amount to the obtained pulse rate peak.

4. The pulse rate detection device according to claim 3, wherein
the disturbance factor is due to a movement of the body surface, and the reducing means reduces the reliability if a movement peak in the frequency domain of the movement of the body surface is equal to or closer than the predetermined amount to the obtained pulse rate peak.

5. The pulse rate detection device according to claim 4, wherein
the disturbance factor is due to variation of light illuminating the body surface, and the reducing means reduces the reliability if a light peak in the frequency domain of the variation of light is equal to or closer than the predetermined amount to the obtained pulse rate peak.

6. The pulse rate detection device according to claim 3, wherein
the disturbance factor is due to variation of light illuminating the body surface, and the reducing means reduces the reliability if a light peak in the frequency domain of the variation of light is equal to or closer than the predetermined amount to the obtained pulse rate peak.

7. A non-transitory computer-readable storage medium storing a pulse rate detection program for causing a computer to realize:
a moving image obtaining function for obtaining a moving image captured by photographing a body surface of a subject;
a pulse rate obtaining function for obtaining a pulse rate of the subject on the basis of change of a pixel value of the body surface in the moving image;
a reliability obtaining function for obtaining reliability of the obtained pulse rate;
a determining function for determining: (1) if the obtained reliability is equal to or greater than a first predetermined reliable criteria and (2) if the obtained reliability is less than the first predetermined reliable criteria and is equal to or greater than a second predetermined reliable criteria that is less than the first predetermined reliable criteria and that a difference between the obtained pulse rate and an immediate past pulse rate is equal to or less than a predetermined reference; and
an output function for outputting the obtained pulse rate, wherein:
the output function outputs the obtained pulse rate when the determining function determines that the obtained reliability is equal to or greater than the first predetermined reliable criteria, or
the output function outputs the obtained pulse rate when the determining function determines that the obtained reliability is less than the first predetermined reliable criteria and is equal to or greater than the second predetermined reliable criteria that is less than the first predetermined reliable criteria and the difference between the obtained pulse rate and the immediate past pulse rate is equal to or less than the predetermined reference,
wherein:
the pulse rate obtaining function obtains the pulse rate from a pulse rate peak in a frequency domain of the obtained moving image, and
the reliability obtaining function obtains the reliability on the basis of a signal-to-noise (SN) ratio of the obtained pulse rate.

\* \* \* \* \*